United States Patent [19]

Bauer et al.

[11] 4,154,769
[45] May 15, 1979

[54] PROCESS FOR THE PRODUCTION OF 2-ALKOXY-4-PROPEN-1-YL-PHENOLS

[75] Inventors: Kurt Bauer, Holzminden; Reiner Mölleken, Golmbach; Rudolf Hopp, Holzminden, all of Fed. Rep. of Germany

[73] Assignee: Haarmann & Reimer GmbH, Holzminden, Fed. Rep. of Germany

[21] Appl. No.: 779,666

[22] Filed: Mar. 21, 1977

Related U.S. Application Data

[63] Continuation of Ser. No. 568,092, Apr. 14, 1975, abandoned.

[30] Foreign Application Priority Data

Apr. 19, 1974 [DE] Fed. Rep. of Germany ....... 2418973

[51] Int. Cl.$^2$ .................... C07C 41/00; C07C 41/10
[52] U.S. Cl. ..................... 568/628; 568/652
[58] Field of Search ..................... 260/613 D

[56] References Cited

U.S. PATENT DOCUMENTS

| | | | |
|---|---|---|---|
| 2,373,982 | 4/1945 | Sturrock et al. | 260/624 B X |
| 2,560,173 | 7/1951 | Johnson et al. | 260/613 R X |
| 2,591,651 | 4/1952 | Young | 260/613 R X |
| 2,829,175 | 4/1958 | Bowman et al. | 260/613 R X |
| 2,862,976 | 12/1958 | Dubbs et al. | 260/613 R X |
| 2,979,534 | 4/1961 | Petropoulos et al. | 260/624 B X |
| 3,281,478 | 10/1966 | Farnham | 260/619 |

FOREIGN PATENT DOCUMENTS

| | | | |
|---|---|---|---|
| 1270749 | 7/1961 | France | 260/624 B |
| 905994 | 9/1962 | United Kingdom. | |

OTHER PUBLICATIONS

Braun et al., Ann, vol. 472 (1929) 72–79.
Quelet, Compt. Rend., vol. 202 (1936) 956–958.

*Primary Examiner*—Bernard Helfin
*Attorney, Agent, or Firm*—Sprung, Felfe, Horn, Lynch & Kramer

[57] ABSTRACT

The invention concerns a new process for the production of 2-alkoxy-4-propen-1-yl phenols of the formula

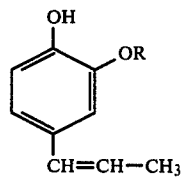

in which R represents the methyl or ethyl radical wherein 2-alkoxy phenols of the formula

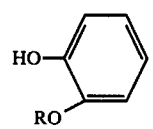

in which R is as defined above, are initially condensed with propionaldehyde in the presence of acid catalysts, and the resulting condensation product is subsequently split by heating in the presence of a basic catalyst to form the phenols of formula I.

7 Claims, No Drawings

PROCESS FOR THE PRODUCTION OF 2-ALKOXY-4-PROPEN-1-YL-PHENOLS

This is a continuation of application Ser. No. 568,092, filed Apr. 14, 1975 and now abandoned.

There are already various processes for producing 2-alkoxy-4-propen-1-yl phenols (isoeugenol and ethyl isoeugenol):

(1) Isomerising eugenol or ethyl eugenol with alkalis (Piscepromisdat 1939, page 303) or under the influence of catalysts, for example nickel, palladium carbon or ruthenium chloride (German Offenlegungsschrift No. 1,936,727).

(2) Reacting vanillin with ethyl magnesium bromide to form guaiacol ethyl carbinol which may be dehydrated in the presence of glycerol and potassium carbonate (Russian Pat. No. 114,197; cf. also CA 53, 1959, 14 140e) or in the presence of aluminium oxide (Russian Pat. No. 126,879, cf. also CA 54, 1960, 19596c) to form isoeugenol.

(3) Working up various plant extracts or lignin with alkalis (Holz, Roh- und Werkstoff 23, 237–40, 1965, ef.C 1966, (28) 1047). But these processes suffer from serious disadvantages.

The present invention relates therefore to a new process for the production of 2-alkoxy-4-propen-1-yl phenols corresponding to the formula (I)

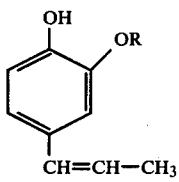

in which R represents the methyl or ethyl radical.

The process according to the invention is characterised by the fact that 2-alkoxy phenols corresponding to the formula (II)

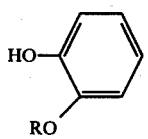

in which R is as defined in reference to formula I, are initially condensed with propionaldehyde in the presence of acid catalysts, and the resulting condensation product subsequently split by heating in the presence of a basic catalyst to form the phenols of formula I.

2-Methoxy phenol and 2-ethoxy phenol are used as starting compounds for the first stage of the process according to the invention.

Acid catalysts suitable for use in the condensation reaction are, in particular, medium-strength to strong proton acids, acid ion exchangers, acid anhydrides of inorganic acids or Lewis acids.

The following are mentioned as examples of medium-strength to strong Proton acids: inorganic acids such as sulphuric acid, acids of phosphorus, for example orthophosphoric acid, pyrophosphoric acid, metaphosphoric acid, polyphosphoric acid, phosphotungstic acid or phosphomolybdic acid, also hydrohalic acids, for example hydrofluoric, hydrochloric and hydrobromic acid, and amidosulphonic acid; strong organic acids such as sulphonic acids, for example p-toluene sulphonic acid, p-methoxy benzene sulphonic acid, also oxalic acid, trifluoroacetic acid and picric acid.

The following are mentioned as examples of acid ion exchangers: inorganic cation exchangers such as natural hydrosilicates of aluminum, for example montmorillonites, glauconites or zeolites, prepared (for example by acid treatment) hydrosilicates of aluminum (cf. Ullmanns Enzyklopädie der technischen Chemie, Vol. 8, 3rd Edition (1957). page 801), mineral cation exchangers produced on a commercial scale from silicates, such as kaolin or feldspar, and alumina minerals, such as bauxite, silica and sodium hydroxide or soda (cf. Ullmann, Vol. 8 3rd Edition (1957), page 802), the aluminum compounds being replaceable either wholly or in part by iron, tin, lead, zirconium, titanium, chromium, tungsten, vanadium or boron compounds (cf. Ullmann, Vol. 8, 3rd Edition (1957), page 802); or carbon-based exchangers activated with sulphuric acid, or organic cation exchangers, for example polycondensation resins based on phenolformaldehyde or polymerisation resins based on styrene or alkyl-, alkoxy- or halogen-substituted styrenes containing carboxyl or phosphoric acid groups, also copolymers of polystyrene, acrylic acid, methacrylic acid or maleic acid containing sulphonic acid, carboxyl or phosphoric acid groups (cf. Ullmann, Vol. 8, 3rd Edition (1957), pages 806–810).

Acid anhydrides of inorganic acids are, in particular, solid acid anhydrides of inorganic non-oxidising acids, for example phosphorus pentoxide.

The following are mentioned as examples of Lewis acids: aluminum chloride, antimony trichloride, antimony pentachloride, iron (III) chloride, boron fluoride, zinc chloride or phosphorus halides, such as $PCl_3$ or $PCl_5$.

It is also possible to use mixtures of the aforementioned catalysts.

The acid catalysts are used in quantities of from 0.001 to 10% by weight, preferably in quantities of from 0.1 to 5% by weight and more especially in quantities of from 0.1 to 3% by weight, based on the weight of propionaldehyde used.

The condensation reaction is carried out at temperatures in the range from about 0° C. to 100° C., preferably at temperatures in the range from 60° C. to 90° C. and, more especially, at temperatures in the range from 65° C. to 85° C.

Basically, the pressure applied is not critical. In general, the reaction is carried out under normal pressure although, in special cases, it may be advantageous to carry out the reaction either under reduced pressure or excess pressure. For example, the water formed during the condensation reaction is easier to remove where the reaction is carried out under reduced pressure, thereby providing for an increase in conversion. On the other hand, the reaction temperature and, hence, the reaction velocity may be increased when the reaction is carried out under excess pressure.

The 2-alkoxy phenols of general formula II are generally used in excess. For example, it is advantageous to react about 3 to 10 mols of the phenol with 1 mol of propionaldehyde. On completion of the reaction, the unreacted phenol may readily be separated off from the condensation product formed, for example by distillation.

In the condensation reaction, 2 mols of alkoxy phenol (II) react with 1 mol of propionaldehyde to form the corresponding 1,1-bis-(hydroxy alkoxy phenyl)- propanes in accordance with the following scheme:

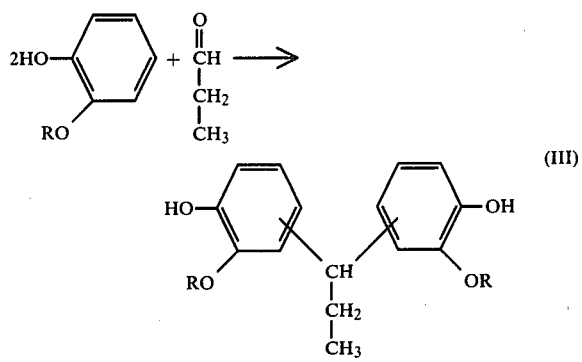

The bis-(hydroxy alkoxy phenyl)-propanes (III) are formed in high yields. Since the H-atom of the benzene nucleus in the p-position to the hydroxy group is preferably substituted by the carbonyl carbon atom of the aldehyde, 1,1-bis-(4-hydroxy-3-alkoxy phenyl)- propanes are the main products. Accordingly, the condensation products consist essentially of 1,1-bis-(4-hydroxy-3-methoxy phenyl)-propane or of 1,1-bis-(4-hydroxy-3-ethoxy phenyl)-propane.

In the second stage of the process according to the invention, these condensation products are subjected to thermal splitting at 180° C. to 250° C., preferably at 210° C. to 240° C., in the presence of a basic catalyst.

Suitable basic catalysts include oxides, hydroxides, alcoholates, phenolates, alkyl carboxylates, carbonates, amides or hydrides of aluminum, zinc, cadmium or lead and, in particular, of alkali metal and alkaline-earth metals.

It has proved to be particularly effective to use alkali metal hydroxides, such as lithium, sodium and potassium hydroxide, and alkali metal alcoholates, such as lithium, sodium and potassium methylate and ethylate. It is preferred to use potassium hydroxide. Mixtures of the aforementiond basic catalysts may also be used.

The basic catalysts are generally used in quantities of from about 0.01% to 10% by weight and preferably in quantities of from 0.1% to 5% by weight, based on the amount of condensation product.

Splitting of the 1,1-bis-(hydroxy alkoxy phenyl)-propanes (III) is carried out under normal pressure or, preferably, under reduced pressure. A reduced pressure of about 0.1 to 700 mm Hg has proved to be effective depending upon temperature. At temperatures in the range from 200° C. to 250° C., for example, it has proved to be particularly effective to apply a reduced pressure of from about 0.1 to 100 mm Hg.

It has also proved to be of advantage to carry out splitting in an inert-gas atmosphere, for example in nitrogen.

To carry out the process according to the invention, the condensation product is heated with the catalyst, and the propenyl phenol (I) formed is distilled off from the reaction mixture together with the 2-methoxy phenol or 2-ethoxy phenol formed at the same time.

Separation of the compound mixture accumulating during splitting is preferably carried out by fractional distillation or recrystallisation from solvents, for example alcohols, such as methanol and ethanol, hydrocarbons such as ligroin cyclohexane, benzene, toluene and xylene or water or mixtures of these solvents.

2-Methoxy-4-propen-1-yl phenol (isoeugenol) is used as an odorant and a flavouring (S. Arctander, Perfume and Flavour Chemicals, Montclair 1969). Isoeugenol is also used as an intermediate product in the preparation of vanillin (German Pat. No. 517,539) and medicaments, for example methyl dopa.

2-Ethoxy-4-propen-1-yl phenol is used as an intermediate product in the production of 4-hydroxy-3-ethoxy benzaldehyde (ethyl vanillin), employed as a flavouring.

The advantage of the process according to the invention over known processes is that it enables 2-alkoxy-4-propenyl phenols to be readily obtained in excellent yields, even on a commercial scale, from readily available starting compounds. When it is taken into consideration that the unreacted starting materials are continuously recycled to the corresponding reaction stages both during condensation an during thermal splitting, an almost complete conversion of the starting compounds is obtained.

The condensation of guaiacol and propionaldehyde and the thermal splitting of the product of condensation in the presence of an acid catalyst, is described in the Dissertation by K. Remesat, Berlin 1931, more especially pages 29, 56 and 58. However, it is propyl guaiacol and not propenyl guaiacol which is obtained by this process.

The production of 4-alkenyl phenols by subjecting bis-(4-hydroxy phenol)-alkanes to thermal splitting in the presence of basic catalysts, is known from British patent specification No. 905,994.

The thermal splitting reaction used in the process according to the invention differs from the splitting reaction described in British patent specification No. 905,994 in that 3-alkoxy-4-hydroxy phenol propanes, i.e. pyrocatechol derivatives, are used in it. It is known from numerous reactions, that the pyrocatechol compounds behave fundamentally differently from the corresponding phenol compounds.

Accordingly, the thermal spitting reaction used in accordance with the invention was not suggested by the spitting reaction described in this British patent specification. Rather had it been expected that dealkylation of the alkoxy group and rearrangement reactions will occur under the described reaction conditions. It has surprisingly been found that these rearrangement reactions do not take place, so that the required 2-alkoxy-4-propen-1-yl phenols are obtained not only in high yields, but also in the commercially interesting trans-form.

EXAMPLE 1

A mixture of 8 mols of guaiacol (2-methoxy phenol), 1 mol of propionaldehyde and 500 g of anhydrous cation exchanger in the H+-form (Lewatit SC 104/H+), was introduced into the reaction vessel equipped with stirrer, thermometer, inlet-tube and outlet-tube. Further quantities of 8:1 guaiacol-propionaldehyde-mixture were introduced via a metering unit through the inlet-tube at a reaction temperature of 55° C. to 70° C. and at such a rate that 525 g/h of reaction product could be removed through the outlet-tube. In order to avoid entrainment of liquid reaction mixture by the off-going product stream the outlet-tube is equipped with a frit at the end facing the reaction vessel.

Following removal of the water of reaction and unreacted guaiacol by distillation at 110° C./10 Torr, 990 g of condensation product, consisting mainly of 1,1-bis-(4- hydroxy-3-methoxy phenyl)-propane, were obtained from 4 kg of reaction product.

600 mg of NaOH were added to 600 g of this condensation product in a distillation apparatus provided with a 30 cm Vigreux column attachment, followed by heating under nitrogen. 500 g of a mixture of guaiacol and isoeugenol of b.p. 110°-140° C./10 Torr, distilled over at a sump temperature of 220 to 240° C./10 Torr.

The isoeugenol can be isolated in pure form from the mixture by fractional distillation at b.p. 140° C.-142° C./13 Torr. The yield of isoeugenol (cis-trans mixture) amounted to 307 g (90% of the theoretical yield, based on the condensate used, and 81% based on the guaiacol consumed). The trans-isoeugenol content of the isomer mixture amounted to 85%-90%.

EXAMPLE 2

A mixture of 1240 g (10 mols) of guaiacol (2-methoxy phenol), 20 g of acetic acid, 300 g of 65% by weight $H_2SO_4$ and 10 g of $\beta$-mercaptopropionic acid, was introduced into a three-necked flask equipped with a thermometer, stirrer and dropping funnel, followed by the addition over a period of 3 hours at 5° C. to 10° C. of 145 g (2.5 mols) of propionalehyde. After stirring for 24 hours at the same temperature, the reaction mixture was extracted with 1 liter of methylene chloride to isolate the condensation product. In addition to methylene chloride and unreacted starting materials, distillation of the organic phase at 110° C./10 Torr gave 424 g of condensation product (b.p. 200°-210° C./0.1-0.5 Torr) which consisted mainly of 1,1-bis-(4-hydroxy-3-methoxy phenyl)-propane, and 12 g of residue. 200 g of the condensation product were heated under nitrogen with 200 mg of KOH in a distillation apparatus provided with a 10 cm Vigreux column attachment. A mixture of guaiacol and isoeugenol (b.p. 100°-140° C./10 Torr) distilled off at a sump temperature of 220° C. to 240° C. Yield of distillate: 117 g (64 g of unsplit condensation produce were recovered from the distillation residue by distillation at b.p. 200°-210° C./0.1-0.5 Torr.) 66.1 of isoeugenol (58% of the theoretical yield, based on the condensate used) were obtained from the 117 g of distillate by fractional distillation at 140°-142° C./13 Torr.

EXAMPLE 3

138 g of 1,1-bis-(4-hydroxy-3-methoxy phenyl)-propane (m.p. 120°-121° C.) were heated under nitrogen with 200 mg of KOH in a distillation apparatus. A mixture of guaiacol and isoeugenol (b.p. 110°-140° C./10 Torr) distilled off at a sump temperature of 220° C.-240° C. Yield of distillate: 115.5 g; distillation residue; 16 g. 65.8 g of isoeugenol were recovered from the distillate by fractional distillation at 140°-142° C. and 13 Torr (corresponding to a yield of 83.8% of the theoretical yield, based on the condensate used).

EXAMPLE 4

545 g of the condensation product of guaiacol (2-methoxy phenol) and propionaldehyde prepared in accordance with Example 1 were heated in a distillation apparatus following the addition of 1 g of LiOH. 365 g of a guaiacol/isoeugenol mixture (b.p. 110° C.-140° C./10 Torr) distilled off at a sump temperature of 220° C.-240° C. The yield of the pure isoeugenol isolated from this mixture by fractional distillation amounted to 58.3% of the theoretical yield.

EXAMPLE 5

(Comparison Example; K. Remesat's method, cf. Dissertation, Berlin, 1931, pages 28,29 and 58).

Following the addition of 5 g of Tonsil AC, 100 g of the condensation product of guaiacol and propionaldehyde prepared in accordance with Example 1 were heated in a distillation apparatus. 90.7 g of product (b.p. 220°-240° C./68 8 Torr) distilled over at a sump temperature of 220° C.-240° C. The distillate consisted predominantly of starting material and a little guaiacol. Distillation residue; 9 g When the sump temperature was increased to beyond 250° C. during splitting, propyl guaiacol, guaiacol and resin-like secondary products were predominantly formed.

EXAMPLE 6

996 g (7 mols) of guaethol (2-ethoxy phenol) and 150 g of anhydrous cation exchanger in the $H^+$ - form (Lewatit SC 102/$H^+$) were introduced into a three-necked flask equipped with a stirrer, condenser, dropping funnel, thermometer, 30 cm Vigreux column attachment and heating system, followed by the addition over a period of 30 minutes at 65° C. of 58 g (10 mols) of propionaldehyde. After stirring for 1 hour at the same temperature, the mixture was filtered off from the ion exchanger and water of reaction, unreacted propionaldehyde and excess guaethol subsequently distilled off at 110° C./10 Torr, leaving 123 g of condensation product consisting mainly of 1,1-bis-(4-hydroxy-3-ethoxy phenyl)-propane.

The 125 g of condensation product were then heated following the addition of 200 mg of NaOH. A mixture of guaethol and p-propen-1-yl guaethol (b.p. 120°-150° C./10 Torr) distilled off at a sump temperature of 220° to 250° C./10 Torr. Yield of distillate: 100g. 48.5 g of pure p-propen-1-yl guaethol were obtained from the distillate by fractional destillation (corresponding to a yield of 70 % of the theoretical yield).

"Lewatit" is a trade mark of Bayer AG.

We claim:

1. A process for the production of a 2-alkoxy-4-propen-1-yl phenol of the formula

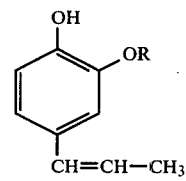

wherein
R is methyl or ethyl,
which comprises condensing a 2-alkoxy phenol of the formula

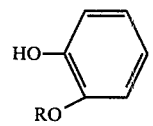

with propionaldehyde in the presence of an acid catalyst, and heating the resulting condensation product to a temperature of 180° to 250° C. in the presence of 0.01 to 10% based on the weight of the condensation product of a basic catalyst selected from the group consisting of alkali metal hydroxides and alcoholates, thereby to split the condensation product.

2. A process as claimed in claim 1, wherein condensation is carried out at temperatures in the range from 0° C. to 100° C.

3. A process as claimed in claim 1, wherein condensation is carried out at temperatures in the range from 60° C. to 90° C. and thermal spitting at temperatures in the range from 210° C. to 240° C.

4. A process as claimed in claim 1, wherein 2-alkoxy phenols and propionaldehyde are used in a molar ratio of 3 to 10:1 for condensation.

5. A process as claimed in claim 1, wherein medium-strength to strong proton acids, acid ion exchangers, acid anhydrides of inorganic acids or Lewis acids, are used as acid catalysts for the condensation reaction.

6. A process as claimed in claim 1, wherein thermal splitting is carried out under reduced pressure.

7. A process as claimed in claim 1, wherein the basic catalyst is present in about 0.1 to 5% by weight of the condensation product.

* * * * *